US011649252B2

(12) United States Patent
Kaufmann et al.

(10) Patent No.: US 11,649,252 B2
(45) Date of Patent: May 16, 2023

(54) ENERGY-EFFICIENT SOLVENT-FREE METHOD FOR PRODUCING METAL CHELATES

(71) Applicant: TECHNISCHE UNIVERSITAT CLAUSTHAL, Clausthal-Zellerfeld (DE)

(72) Inventors: Dieter E. Kaufmann, Goslar (DE); Jan C. Namyslo, Herzberg am Harz (DE); Roman Florescu, Goslar (DE); Birgit Wawrzinek, Clausthal-Zellerfeld (DE)

(73) Assignee: TECHNISCHE UNIVERSITAT CLAUSTHAL, Clausthal-Zellerfeld (DE)

(*) Notice: Subject to any disclaimer, the term of this patent is extended or adjusted under 35 U.S.C. 154(b) by 250 days.

(21) Appl. No.: 16/606,531

(22) PCT Filed: Jan. 8, 2018

(86) PCT No.: PCT/EP2018/050343
§ 371 (c)(1),
(2) Date: Feb. 11, 2020

(87) PCT Pub. No.: WO2018/192686
PCT Pub. Date: Oct. 25, 2018

(65) Prior Publication Data
US 2021/0309674 A1 Oct. 7, 2021

(30) Foreign Application Priority Data
Apr. 21, 2017 (DE) ............ 10 2017 108 611.0

(51) Int. Cl.
| | | |
|---|---|---|
| C07F 1/08 | (2006.01) | |
| A23K 20/142 | (2016.01) | |
| A23K 20/20 | (2016.01) | |
| A23L 33/165 | (2016.01) | |
| A23L 33/175 | (2016.01) | |
| A01N 55/02 | (2006.01) | |
| A61K 31/30 | (2006.01) | |
| A61K 31/315 | (2006.01) | |
| B01J 8/24 | (2006.01) | |
| B01J 31/22 | (2006.01) | |
| C05C 11/00 | (2006.01) | |
| C07F 3/06 | (2006.01) | |

(52) U.S. Cl.
CPC ............ *C07F 1/08* (2013.01); *A01N 55/02* (2013.01); *A23K 20/142* (2016.05); *A23K 20/30* (2016.05); *A23L 33/165* (2016.08); *A23L 33/175* (2016.08); *A61K 31/30* (2013.01); *A61K 31/315* (2013.01); *B01J 8/24* (2013.01); *B01J 31/2217* (2013.01); *C05C 11/00* (2013.01); *C07F 3/06* (2013.01); *A23V 2002/00* (2013.01)

(58) Field of Classification Search
CPC ......... A61K 31/30; A61K 31/315; B01J 8/24; B01J 31/2217
See application file for complete search history.

(56) References Cited

U.S. PATENT DOCUMENTS

| | | |
|---|---|---|
| 2,877,253 A | 3/1959 | Rummer et al. |
| 5,702,718 A | 12/1997 | Ridenour |
| 6,426,424 B1 | 7/2002 | Ashmead et al. |
| 6,518,240 B1 | 2/2003 | Pedersen et al. |
| 9,346,830 B2 | 5/2016 | Ramhold et al. |
| 2009/0042850 A1 | 2/2009 | Basnakian et al. |
| 2015/0342851 A1 | 12/2015 | Liu et al. |

FOREIGN PATENT DOCUMENTS

| | | |
|---|---|---|
| DE | 10 2004 039 486 A1 | 2/2006 |
| DE | 10 2011 011 924 A1 | 8/2012 |
| EP | 2 204 099 A1 | 7/2010 |
| EP | 2 389 670 | 11/2011 |

(Continued)

OTHER PUBLICATIONS

Chan et al: "Ultrafine Grinding Using a Fluidized Bed Opposed Jet Mill: Effects of Feed Load and Rotational Speed of Classifier Wheel on Particle Shape", Drug Development and Industrial Pharmacy, vol. 28, No. 8, pp. 929-947, 2002.

(Continued)

*Primary Examiner* — Kevin E Weddington
(74) *Attorney, Agent, or Firm* — WCF IP

(57) ABSTRACT

The invention relates to a method for producing, amongst other things, amino-acid and/or hydroxycarboxylic-acid metal chelates, a solvent-free mixture of at least one metal oxide, metal hydroxide, metal carbonate or oxalate, and the solid organic acid is subjected to intensive mechanical stress. According to the invention, this is done in that the reaction partners are introduced in particle form into a fluid stream of a fluid-bed countercurrent mill operating without grinding elements, wherein mechanical activation of at least one of the reaction partners is effected by collision processes within a reaction chamber formed in a region of the fluid stream, and a solid body reaction to form the metal chelate is triggered. The novel method operates very energy-efficiently and with a high specific yield. It leads to a product having compact particles in the small, single-digit micrometer range having a comparatively narrow particle size distribution and a large surface. The product is homogenous and very pure. Thermal loading or decomposition of the organic chelate ligands, in particular of the amino acids, is likewise avoided, as are contaminants from milling and grinding element abrasion.

8 Claims, 10 Drawing Sheets

(56) References Cited

FOREIGN PATENT DOCUMENTS

Figure 1A:
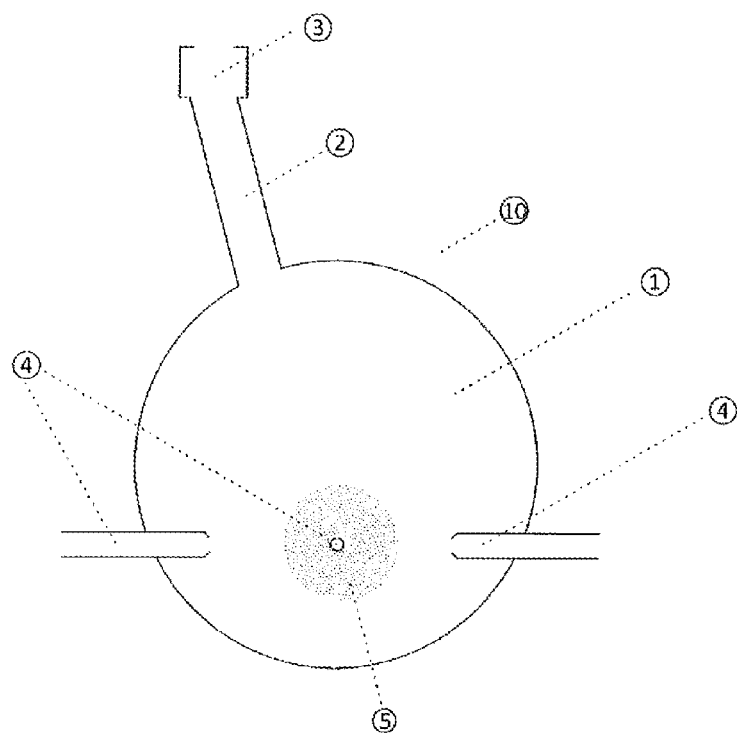

| | | |
|---|---|---|
| EP | 2 489 670 A1 | 8/2012 |
| WO | 2004/075654 A1 | 9/2004 |
| WO | 2006/069419 A1 | 7/2006 |
| WO | 2010/085505 A1 | 7/2010 |
| WO | 2010/144817 A1 | 12/2010 |
| WO | 2012/110063 A1 | 8/2012 |
| WO | 2013/110789 A1 | 8/2013 |
| WO | 2014/185824 A1 | 11/2014 |

OTHER PUBLICATIONS

Wang et al: "Dry Comminution of Silicon Carbide Particles in a Fluidized Bed Opposed Jet Mill: Kinetics of Batch Grinding", Particulate Science and Technology, vol. 28, pp. 566-580, 2010.

Heng et al: "Ultrafine grinding using a fluidized bed opposed jet mill: effects of process parameters on the size distribution of milled particles", S.T.P. Pharma Sciences, vol. 10, No. 6, pp. 445-451, 2000.

Wang et al: "Parameter effects on dry fine pulverization of alumina particles in a fluidized bed opposed jet mill", Powder Technology, vol. 214, pp. 269-277, 2011.

Korzen et al: "Problems of design synthesis and testing of fluidized bed jet mills", Zeszyty Naukowe—Politechnika Lodzka, Inzynieria Chemiczna I Procesowa, vol. 22, pp. 141-150, 1997.

Wilson et al: "Structural Characterization of Bis(L-methionato)zinc(II), Zn(L-met)2", Inorganic Chemistry, vol. 16, No. 6, pp. 1498-1502, 1977.

Liu et al: "Thermal Behaviour of the Complexes on Zinc Amino Acids", vol. 58, pp. 323-330, 1999.

Zhang et al: "Fluidized-bed Jet Mill for Controlling Granule Morphology of Ultra-Fine SiC", Rev. Adv. Mater. Sci. vol. 33, pp. 77-84, 2013.

Nair et al: "Energie-effizientes Iosungsmittelfreies Verfahren zur Herstellung von Aminosaure-metallchelaten", World Congress on Particle Technology 3, pp. 1514-1526, 1998.

Rockwell et al: "Fluid Energy Grinding", Ceramic Bullet, vol. 44, No. 6, pp. 497-499, 1965.

Rombach et al: "Coordination modes of aminoacids to zinc", Inorganica Chimica Acta, vol. 334, pp. 25-33, 2002.

Benz et al: "Performance of a fluidized bed jet mill as a function of operating parameters", Int. J. Miner. Process, vol. 44-45, pp. 507-519, 1996.

Berthiaux et al: "Modelling fine grinding in a fluidized bed opposed jet mill Part I: Batch grinding kinetics", Powder Technology, vol. 106, pp. 78-87, 1999.

Berthiaux et al: "Modelling fine grinding in a fluidized bed opposed jet mill Part II: Continuous grinding", Powder Technology, vol. 106, pp. 88-97, 1999.

Su et al: "Jet grinding and surface modification of ZnO nanoparticles", Guangzhou Huagong, vol. 40, No. 10, pp. 101-102, 2012.

Su et al: "Novel Surface Modification of ZnO Nanoparticles by Fluidized-Bed Jet Mill", Journal of Advanced Microscopy Research, vol. 9, pp. 54-57, 2014.

ENERGY-EFFICIENT SOLVENT-FREE METHOD FOR PRODUCING METAL CHELATES

The invention relates to the efficient preparation of metal chelates, in particular amino acid-metal chelates and hydroxycarboxylic acid-metal chelates, in which a dry, namely solvent-free, mixture of at least one metal compound from the group consisting of metal oxide, metal hydroxide and metal salt and at least one solid organic acid which comprises at least one chelating acid from the group consisting of alpha- and beta-amino acids and hydroxycarboxylic acids is subjected to intensive mechanical stress in order to produce the chelate complexes mentioned. The invention further relates to the corresponding metal chelate compositions as are obtainable by means of this process, the use thereof and also further compositions which contain the process product or the metal chelate compositions according to the invention.

Chelates or synonymously chelate complexes are coordination compounds in which at least one polydentate ligand, hereinafter referred to as chelating ligand or "chelator", occupies at least two coordination or bonding positions on a central atom. In a chelate complex, one or more chelators can be present per central atom. The central atom is a positively charged metal ion of metals such as, inter alia, zinc (Zn), copper (Cu), manganese (Mn), selenium (Se), iron (Fe), calcium (Ca), magnesium (Mg), nickel (Ni), cobalt (Co), vanadium (V), chromium (Cr) and molybdenum (Mo). In the chelate, some metals occur as cations in only one valence (e.g. $Zn^{2+}$) while others (e.g. those of Cu, Fe, Ni, Co, V, Cr or Mo) occur in a plurality of valences or as oxo cations, for example molybdenum oxo cations in the oxidation states +IV, +V and +VI and vanadium usually in the form of vanadyl, $VO^{2+}$.

It has been known for a long time that trace elements and trace element compounds are present in small amounts ("in traces") in animal, human or vegetable organisms and often fulfill functions which are important to life, which can be seen from the fact that a deficiency of them leads to manifestation of deficiency or disease symptoms, to general weakness and/or to a reduced reproduction rate. Being able to supply these elements in a suitable administration form is therefore of great interest.

Using one (or more) organic acid anions which contain additional electron donor groups (—$NH_2$, —OH), in particular amino acid anions, as chelate complex partners of the respective metal and thus utilizing, in addition to the trace element, the amino acids and/or hydroxycarboxylic acids which are in any case frequently administered as supplements with their positive physiological action in the form of a slightly bioavailable complex is also known and is customary practice (see, for example, K. W. Ridenour, U.S. Pat. No. 5,702,718 (A), 1997 and patents cited therein).

In general, not only natural amino acids but any organic acids bearing amino and/or hydroxy groups, preferably with these substituents in the alpha or beta position relative to the carboxyl unit, are generally suitable for preparing these metal chelates. However, preference is given to using the naturally occurring amino acids alanine, arginine (basic), aspartene, aspartic acid (acidic), cysteine, glutamine, glutamic acid (acidic), glycine, histidine (basic), isoleucine, leucine, lysine (basic), methionine, phenylalanine, proline, serine, threonine, tryptophan, tyrosine and valine.

A suitable method for preparing such compounds, which are widely used, for example as additives in the human sector and in animal nutrition, is of great general interest.

The chelate stability should not have an adverse effect on the bioavailability of the amino acid or hydroxycarboxylic acid. Many amino acid chelates even increase the bioavailability of the central cation coadministered compared to a salt or oxide of this cation.

As has now been shown by scientific studies, biosorption from particular chelate compounds in the human or animal organism is particularly effective. The amino acid chelates with their moderate strength of chelating via the nitrogen atom display a particularly high bioavailability. As is well documented in the literature and known to those skilled in the art, a significantly higher bioavailability of the metals has often been found when they are used in the form of their chelates than is the case when using corresponding inorganic metal salts.

According to the present-day state of the art, the production of suitable amino acid-metal chelates as organic trace element compounds is mainly carried out with only low energy efficiency by wet chemical means or else by likewise energy-intensive mechanical processes with participation of milling media, especially in ball mills, within the latter case about 90% of the energy supplied being merely converted into heat (see EP 2489670 A1). The known wet-chemical processes are burdened by, in particular, the unavoidably energy-inefficient and correspondingly costly drying of the material; in addition, the product is not free of foreign inorganic anions.

Solvent-free processes, inter alia, are also known from the prior art (Rummel, U.S. Pat. No. 2,877,253 (A), 1959; Ashmead, Pedersen, U.S. Pat. No. 6,426,424 (B1), 2002; Pedersen, Ashmead, U.S. Pat. No. 6,518,240 (B1), 2003). Although solvent-free processes do not per se have the abovementioned disadvantage that large amounts of the solvent, normally water, have to be removed, they do however require additional amounts of energy when product formation occurs in mechanical mills containing milling media, especially in ball mills. The reason for the increased energy consumption is that milling media have to be set in motion as additional masses, for example in the process described by D. Ramhold, E. Gock, E. Mathies, W. Strauch, EP 2489670 (A1), 2012, in an excentric vibratory mill (EVM). When excentric vibratory mills are used, the energy consumption for driving the counterweight is additional. Furthermore, in such an inhomogeneously operating vibratory mill system, comparatively high wear is observed as a result of the high impact stresses on the milling media themselves. The abraded material is then undesirably found in the product.

In addition, the drying of material mentioned at the outset also becomes relevant in the last-named processes since water of reaction formed in this type of reaction milling has to be removed again under action of heat and/or with reduction of the pressure, with additional energy consumption.

A further disadvantage of the abovementioned solid-state processes for producing metal chelates is the sometimes considerable size heterogeneity and structural heterogeneity of the solid products obtained. Thus, for example, the process described in EP 2 489 670 A1 produces acicular metal-amino acid chelate structures having an average particle size of from 40 to 60 µm, with up to 80% of the particles having a particle size from >0 to 100 µm and up to 2% have a particle size of more than 500 µm, i.e. a value which is a factor of 10 higher than the "average size" of 50 µm, thus with a considerable amount of oversize particles.

A great structural heterogeneity quite generally increases the difficulty of further processing of the metal chelate complexes obtained, for example classification according to particle size, precise metering and homogeneous mixing with further substances. The active compound release kinetics are also unfavorably influenced by the particle size heterogeneity. A greatly acicular morphology hinders the flowability and scatterability of the particulate product. Acicular crystals of the complexes with are not readily water-soluble and sometimes even acid-insoluble can be hazardous to health when absorbed in the human or animal body. Acicular structures are therefore to be avoided.

It is therefore an object of the invention to avoid the disadvantages of the prior art in respect of the production process as far as possible and to provide metal chelates having a different morphology. An energy-efficient process giving a good yield and having a high selectivity should be made available here. By-products and decomposition products, in particular of the organic complexing ligands, should be avoided.

The starting materials for the process are present in the solid state. The nature of the particles of the starting materials can correspond to a finely particulate or finely crystalline, commercial form normal for the material. Premilling of the starting materials is generally not necessary. The metal oxides used, e.g. zinc oxide and copper oxide, are available with particle sizes in the range from, for example 150 to 300 μm and can be used in this form. The solid organic acids are commercially available with particle sizes of from about 200 to 500 μm and can likewise be used directly as obtained, i.e. in commercial particle sizes.

To provide the central atom, metal compounds selected from the group consisting of: metal oxides, metal hydroxides, including mixed oxides and mixed hydroxides, inorganic metal salts and organic metal salts are used. For the chelate ligands, i.e. as chelating organic acids, use is made of amino acids and/or hydroxycarboxylic acids. Further ligands which are not bidentate can be included. The starting materials can be used in premixed form or they can be introduced individually into the fluidized-bed opposed-jet mill serving as reactor and be mixed in a separate apparatus or directly in the milling space of the mill. Metal oxides, metal carbonates and metal oxalates are preferred as metal compound.

According to the invention, the reactants, i.e. at least the metal compound used and the organic acid, are introduced in particulate form into a fluid jet of a fluidized-bed opposed-jet mill operating without milling media. It is important that all reactants are fed into a collision zone in the milling space in which sufficient excitation of the reactants and the activation energy for the desired complexing reaction are provided by particle-particle impacts in the milling gas jet and especially in the center of these nozzle jets. This occurs during use according to the invention of the fluidized-bed opposed-jet mill primarily in the same zone in which the "milling" (here "jet milling"), i.e. the comminution of the solid particles which may additionally take place here too, takes place in the conventional use. The milling space comprises the reaction zone and forms a reaction space for the reactive milling or reaction milling taking place here. The process can be carried out continuously by continuously feeding in the reactants. The fluidized-bed opposed-jet mills to be used require not only far less energy than mills using milling media but also less energy than conventional jet mills in which the milling stock is introduced together with the milling gas stream into the milling space and frictional processes between milling stock and mill wall take place. In addition, the fluidized-bed opposed-jet mill therefore operates virtually without wear (in contrast to classical ball mills and also to a conventional jet mill).

In summary, it may be said that mechanical activation of at least one of the reactants is brought about by particle collision processes within a reaction space formed in a jet region of the fluid jet or a plurality of fluid jets, and a solid-state reaction to form the metal chelate is triggered.

The process is based on acceleration of particles by means of a milling gas stream at high pressure and subsequent collision of these particles, in particular in the focus of milling gas jets directed toward one another. The corresponding collisions lead to such a high energy input that the respective organic acid and the metal source used react to form a chelate.

Here, the oxygen of the metal component forms pure water which at the high air speeds of the process is discharged together with the milling gas stream. Accordingly, no additional energy has to be expended for this purpose.

As regards product formation, it is assumed that the particle collisions, particularly in the center of the gas jets, triggered by jet velocities of usually from 300 m/s to 1000 m/s, lead to lattice defects resulting from the point loadings described. Even at room temperature and a gauge pressure of 6 bar, milling gas velocities of 500 m/s are attained. The abovementioned lattice defects are probably present primarily in the metal compound used having a high specific gravity and make the subsequent reaction to form the amino acid-metal chelate possible. Prior energy-intensive activation, as in the case of corresponding reaction milling processes in an excentric vibratory mill (e.g. as described by D. Ramhold, E. Gock, E. Mathies, W. Strauch, EP 2489670 (A1), 2012), is not necessary, which means a further energy saving. High values of the indicated milling gas velocities, with a corresponding advantage for the extent of particle-particle collisions in the milling space of the fluidized-bed opposed-jet mill, are achieved particularly when the milling gas, which is naturally obtained hot from the compressor, is not cooled with consumption of energy (as is otherwise customary) but instead is used directly as hot gas.

The metal chelate can be a "pure" chelate produced from one metal compound and one amino or hydroxycarboxylic acid or a mixed product in the case of which metal oxides of various metals and/or a plurality of different acids are used in admixture.

The product is collected in a product filter installed downstream of the fluidized-bed opposed-jet mill.

The disadvantages of the processes known from the prior art which are disadvantageous from a process engineering and/or energy point of view can be avoided in this way. The invention is based on the recognition that fluidized-bed opposed-jet mills originally designed for very fine milling allow such a high energy input into the milling stock that, when the starting materials and operating conditions are chosen appropriately, a mechanochemical reaction occurs solely by collision of particles of the material with one another without participation of milling media or other frictional surfaces being necessary.

In contrast thereto, such a solid-state reaction is, in cases known hitherto from the literature, triggered by collision with milling media in ball mills (centrifugal mills, excentric vibratory mills, see, for example, D. Ramhols, E. Gock, E. Mathies, W. Strauch, EP 2489670 (A1), 2012). Mechanisms of such mechanochemical reactions are assumed to be generally tremadous point loadings associated with high local temperatures (see, for example, B. V. Boldyrev, K. Meyer, Festkörperchemie, VEB Verlag für Grundstoffindustrie, Leipzig, 1973; D. Margetic, V. Strukil, Mechanochemical Organic Synthesis, Elsevier Science Publishing Co. Inc., 2016). The temperature-sensitive organic ligands, namely the amino acids and/or hydroxycarboxylic acids here, can be subject to undesirable degradation reactions in such processes.

In the present case according to the invention, on the other hand, no milling media are present. Since, correspondingly, no additional masses have to be set in motion, considerable quantities of energy can be saved in this way. In addition, the resource-conserving process according to the invention in a fluidized-bed opposed-jet mill has the advantage that the end product is free of corresponding abraded metal because of the above-described absence of (steel) milling media. The organic ligands are likewise subjected only to mild conditions. The tendency for secondary and degradation reactions to occur within the ligands is drastically reduced since no heat input occurs in the process, neither for a thermal reaction nor as a result of strong mechanical activation by means of the mass of milling media.

Since the process is carried in the absence of solvent, the associated solvent contamination is absent, both in the production process and in the product. No thermal stressing of the product caused by hot drying occurs. The problematical industrial use of salt solutions is likewise dispensed with, as is the disposal of considerable amounts of residual salts as coproducts. The process products are, due to the synthesis, preferably free of sulfur and sulfates and generally free of salt anions which are not required in the process.

According to the invention, use is made of a fluidized-bed opposed-jet mill in which the particle collisions take place in the center of a plurality of fluid nozzles directed toward one another. Here, an opposed-jet arrangement is any arrangement in which the opposed-jet principle is employed, regardless of the specific angle between the fluid nozzles or milling gas nozzles. The fluid nozzles or milling gas nozzles can preferably be arranged at an angle of from 180° to 60° relative to one another with the jets from the "opposed-jet nozzles" having to cross in order to create a collision space which according to the invention is utilized as reaction space.

In a preferred embodiment, a fluidized bed which provides the reaction space for chelate formation is formed in a fluid stream section in a crossing region of the jet direction of at least two fluid nozzles together with the particulate reactants introduced. From two to six fluid nozzles operating in the opposed-jet mode are at present considered to be preferred, more preferably from two to four fluid nozzles or milling gas nozzles.

In preferred embodiments, the fluidized-bed opposed-jet mill is operated at flow velocities of from about 100 to 1000 m/s, preferably from 250 to 1000 m/s, more preferably 300-1000 m/s, in particular from 300 to 700 m/s, and a milling gas pressure of from about 5 to 10 bar, preferably from about 7 to 8 bar.

The reactants provided at the inlet of the mill or for feeding into the mill, i.e. the solid particulate metal hydroxide, metal carbonate or metal oxalate and the solid amino and/or hydroxycarboxylic acid(s), are fed in as "reaction material" instead of the conventional pure milling stock. This preferably occurs, in general from one or more stock vessels (reservoir(s)), alternatively batchwise from sacks, by means of an independent feed device, for example a shaft or a feed conduit with or without additional transport means.

The use of a fluidized-bed opposed-jet mill means that the reaction material is introduced directly into the milling space; in this way, the gas introduced through the nozzles is itself kept free of particles of the starting material, which could otherwise cause wear and abrasion there, as is the case in conventional jet mills as a result of transport of material through the nozzles and especially in classical mills using milling media (in particular ball mills).

In a particularly preferred embodiment, the reactants are transported by means of a transport device into the milling chamber and reach the reaction space in the interior of the milling chamber in free fall. The transport device preferably has at least one transport screw.

The particle size of the end product can be set by choice of the operating conditions of the fluidized-bed opposed-jet mill together with the classifier wheel which is usually also mounted as standard for very fine milling, usually to the medium to small one-figure micron range (average diameter determined in the manner customary in the art, for example by means of laser light scattering).

The process product is compact and finely particulated. The compact structure is virtually free of crystal needles and there are no appreciable proportions of oversized particles. More than 80% of the particles have an ellipsoidal or cuboidal structure in which the ratio of the longest to shortest particle diameter is less than 4:1. Owing to the compact, finely particulate structure, there is furthermore a comparatively large surface area which has, for example, a positive effect on the scatterability or flowability of the product, the dry miscibility, the dispersibility and the metering accuracy and also the pharmaceutical properties, where appropriate, of products. The process products can thus be incorporated more readily into mixtures and compacts and are more uniformly distributed in these.

The product is obtained in a particularly finely divided form with a narrow particle size distribution. The latter can, for example, be seen from the ratio of the D values, $D_{99}$, $D_{90}$, $D_{50}$, ($D_{10}$). The D value indicates the percentage of particles smaller than the diameter given as the respective D value. The percentage is given as index, i.e.: $D_{90}$= . . . means "90% of the particles have a (volumetrically determined) diameter of less than . . . ". The associated data are obtained by means of laser light scattering.

Compared to known energy-intensive solid-state processes using milling media, a particularly compact and homogeneous particle size is achieved. Thus, for example, the acicular chelate particles described in the patent application EP 2389670 A1 and depicted in an electron micrograph have an average particle size of 40-60 μm, with up to 80% of the particles being in the range 0-100 μm, which corresponds to a D80 value of 100 μm. In comparison, in the case of the invention a very steep, far more homogeneous and better defined particle size distribution is achieved and the particles are overall more than one order of magnitude smaller with an average particle diameter of usually from 1.5 to 3.5 μm (instead of from 40 to 60 μm in the case of ESM processes, see above). This is advantageous for further process steps, in particular mixing of defined amounts of chelate with defined amounts of further substances, since a homogeneous particle size distribution makes processing by machine considerably easier. The risk of lump formation is reduced, and the mechanical components of classification, measuring, metering and dispensing plants can be better matched to a particular chelate crystal size. Particular after-processing steps, e.g. milling of the chelate crystals obtained to achieve a homogeneous, sufficiently small particle size, can be dispensed with.

It is frequently the case that very small amounts of the metal-acid chelates are mixed with, for example, 1000 times their amount of other materials, e.g. in animal fodder or when used as catalyst. In order to be able to add a defined amount of chelates and mix them homogeneously with other materials, a homogeneous, clearly defined particle size of the chelates is very advantageous.

The process product according to the invention is obtained in the form of compact crystals, i.e. virtually needle-free and without an appreciable proportion of over-sized particles. When administered to human beings or animals, the harmful effects on health to be feared in the case of the acicular chelate crystals obtained according to the prior art no longer occur.

It must be emphasized that the reaction milling according to the invention in a fluidized-bed opposed-jet mill occurs completely autogenously and in such a way that the entire energy for product formation including the necessary activation energy is provided exclusively by the gas jet. A temperature increase does not have to be effected from the outside, nor does an uncontrolled temperature increase (which may possibly damage the product) take place in the materials used, as is the case in classical reaction milling operations with ongoing process, predominantly by impact and friction of the milling media themselves. Furthermore, the process of the invention has the advantage that a fluidized-bed opposed-jet mill allows, in contrast to reaction milling in a classical ball mill, usually excentric vibratory mill, continuous operation of the process and thus an increased throughput at a lower specific energy consumption.

A comparative calculation of the respective specific energy consumption in an excentric vibratory mill (single-module, ESM 504, from Siebtechnik GmbH, Mülheim an der Ruhr) and in a fluidized-bed opposed-jet mill (CGS 71, from Erich NETZSCH GmbH & Co. Holding KG, Selb) is given in the following section:

Excentric vibratory mill ESM 504:
Power (dry+mixer): 27.5 KW
Throughput: 40 kg/h
Milling media: Cylpeps 32 mm×32 mm (steel)
Specific energy consumption [KWh per metric ton]: 27.5 KW/40 kg/h×1000 kg=688 KWh/t
Fluidized-bed opposed-jet mill CGS 71:
Air flow: 1920 $m^3$/h (8 bar, 20° C.; ISO 1217)
Power for classifier wheel: 15 KW
Compressor power (1956 $m^3$/h, main drive+sep. fan): 206 KW
Throughput: 500 kg/h
Specific energy consumption [KWh per metric ton]:
221 KW/500 kg/h×1000 kg=442 KWh/t In contrast to the fluidized-bed opposed-jet mill, only batch operation is possible in the case of an excentric vibratory mill.

The specific energy consumption per metric ton of product in the case of the use according to the invention of a fluidized-bed opposed-jet mill is thus more than one third below the consumption of a conventional product plant for amino acid-metal chelates based on an excentric vibratory mill. Furthermore, the present process is characterized by dispensing with catalytically active reagents (such as iron ions) and (in terms of energy) avoiding complicated preceding or subsequent process steps (e.g. spray drying).

The invention thus now makes available an efficient solvent-free process for preparing complexes of chelate-forming metals such as preferably zinc, copper, manganese, selenium, iron, calcium, magnesium, nickel, cobalt, vanadium, chromium or molybdenum, preferably zinc, copper and selenium, with solid organic acids, preferably naturally occurring amino acids, preferably glycine, methionine, lysine and/or cysteine, but also alanine, arginine, aspartene, aspartic acid, glutamine, glutamic acid, histidine, isoleucine, leucine, phenylalanine, proline, serine, threonine, tryptophan, tyrosine and valine. In general, all chelate-forming amino acids and/or hydroxycarboxylic acids, both of synthetic and natural origin, are suitable.

The reaction is achieved solely by a mixture of the respective metal compound, preferably in the form of the oxides (in particular ZnO, CuO, $Fe_2O_3$, $Mn_2O_3$ or corresponding oxides of other metals desired for the products produced or else in the form of oxalates or carbonates of the selected metals for the compounds to be prepared, commixed with the solid inorganic acid (preferably with participation of at least one amino acid), as indicated above, being subjected to mechanical stress in a fluidized-bed opposed-jet mill.

The reaction conversion in the course of the mechanochemical solid-state reaction depends on the operating conditions relevant to the invention in the fluidized-bed opposed-jet mill (i.e. on the milling gas flow and milling gas pressure, on the type and temperature of the milling gas or fluid, preferably air, optionally also nitrogen, argon, carbon dioxide or steam, and on the classifier rotational speed and on the amounts of starting materials introduced). The entry velocity of the gas introduced, thus in particular also geometry, dimensions and arrangement of the jet nozzles, and the degree of accumulation of the reaction milling stock in the reaction chamber are also critical for occurrence of the solid-state reaction.

Suitable fluidized-bed opposed-jet mills are, inter alia, standard in industry for contamination-free comminution and have in principle been known for a long time (see, for example, P. M. Rockwell, A. J. Gitter, Am. Ceram. Soc. Bull. 1965, 44, 497-499). Since about 20 years ago, the development and optimization of such fluidized-bed opposed-jet mills have again been intensively researched (see, for example, P. B. Rajendran Nair, S. S. Narayanan, From World Congress on Particle Technology 3, Brighton, UK, Jul. 6-9, 1998 (1998), 2583-2595; M. Benz, H. Herold, B. Ulfik, Int. J. Min. Proc. 1996, 44-45, 507-519; Z. Korzen, R. Rink, A. Konieczny, Zeszyty Naukowe—Politechnika Lodzka, Inzynieria Chemiczna i Procesowa 1997, 22, 141-150; H. Berthiaux, J. Dodds, Powder Technol. 1999, 106, 78-87; H. Berthiaux, C. Chiron, J. Dodds, Powder Technol. 1999, 106, 88-97). Fine or very fine milling frequently tries to get down to the one figure micron range, with application to pharmaceutical products frequently being the main consideration in optimization of the parameters (see, for example, P. W. S. Heng, L. W. Chan, C. C. Lee, S.T.P. Pharma Sciences 2000, 10, 445-451 or L. W. Chan, C. C. Lee, P. W. S. Heng, Drug Development Ind. Pharm. 2002, 28, 939-947).

The considerable possible energy input is reflected for example, in the possible comminution even of very hard materials including, for example, silicon carbide or aluminum oxide (Y. Wang, F. Peng, Part. Sci. Technol. 2010, 28, 566-580; Y. Wang, F. Peng, Powder Technology 2011, 214, 269-277; M. X. Zhang, H. Y. Chen, C. P. Yan, L. Y. Lin, Rev. Adv. Mat. Sci. 2013, 33, 77-84).

The actual course of a chemical reaction, characterized by the breaking and subsequent reformation of chemical bonds, and thus a reaction milling under the operating conditions of fluidized-bed opposed-jet mills has previously never been utilized in the manner of the invention. An example of surface modification of ZnO nanoparticles may be found in: X. Su, Z. Cao, Q. Li, Z. Zhang, J. Adv. Microscopy Res. 2014, 9, 54-57 and in: X. Su, S. Xu, T. Cai, Guangzhou Huagong 2012, 40, 101-102, both on the subject of "jet grinding/jet milling" and surface modification.

The invention leads to process products having new, hitherto unattainable product properties and encompasses a structurally homogeneous product which is novel in this form and has a very narrow particle size distribution. The finely particulate nature of the product is also worthy of particular emphasis.

The object of the invention is accordingly also achieved by a metal chelate composition containing at least one metal chelate compound having a polyvalent metal cation and at least one chelate ligand which comprises at least one chelating acid from the group consisting of alpha- and beta-amino acids and hydroxycarboxylic acids, wherein the compound is present in the form of particles having a particle size in the one-figure micron range, i.e. an average particle diameter of 5 μm ($D_{50}$=1 to 5 μm), as described above in connection with the process.

The metal chelate composition contains at least one metal chelate compound or consists thereof.

The invention encompasses metal chelate compounds which are obtained directly as process products from the process of the invention, i.e. the pure metal chelate compounds formed on the basis of the stoichiometric composition of the starting materials, and also comprises compositions which contain not only these metal chelate compounds but also other materials which can be first and foremost residual starting materials or be additives or further materials which supplement the composition and have been introduced into the mill during the process.

The metal chelate compound is a coordination compound (also referred to as complex compound, complex) as described above having at least one central atom formed by a polyvalent, i.e. at least divalent, metal cation and at least one chelate ligand which comprises at least one organic, chelating, i.e. at least bidentate in respect of complexation, organic acid selected from the group consisting of alpha- and beta-amino acids and hydroxycarboxylic acids. The amino acids can be natural amino acids, in particular essential amino acids, or else bidentate synthetic amino acids.

The presence of other ligands in addition to the ligands specifically mentioned and claimed, namely other bidentate or monodentate ligands and/or monovalent or polyvalent anions, in the metal chelate compound is not ruled out according to the invention. This can, for example, be desired in order to broaden the range of uses of the metal chelate compositions of the invention.

A preferred complexing acid which can be incorporated in addition to at least one amino acid or hydroxycarboxylic acid as ligand in the chelate complex is nicotinic acid. The associated products are amino acid-nicotinic acid-metal chelates, e.g. copper-nicotinate-glycinate or selenium-nicotinate-methionate.

The metal chelate compounds and metal chelate compositions according to the invention are dry, solid, particulate materials or products having a characteristic structure and size distribution.

In particularly characteristic embodiments, the metal chelate compound is present in the form of particles of which 90% have an average particle diameter (individual particle diameter) of not more than 15 μm and 50% have an average particle diameter (individual particle diameter) of not more than 5 μm ($D_{90}$≤15 μm; $D_{50}$≤5 μm). The average particle diameter (average over all particles in a sample) is in the range from 1 μm to 5 μm for these embodiments.

Typical $D_{50}$ values for individual samples are in the range from 1.5 to 4.5 μm.

Typical $D_{90}$ values for individual samples are in the range from 4 to 6 μm. $D_{90}$ is preferably less than or equal to 15 μm and $D_{90}$ is more preferably 7 μm. Typical $D_{99}$ values for individual samples are in the range from 8 to 15 μm. $D_{99}$ is preferably less than or equal to 20 μm and $D_{99}$ is more preferably 15 μm. There are no oversized particles based on these values since the largest particles according to the invention have sizes which are still below 25 μm ($D_{99.9}$≤25 μm, equating or a sieve exclusion limit of <25 μm).

Figure 2A:
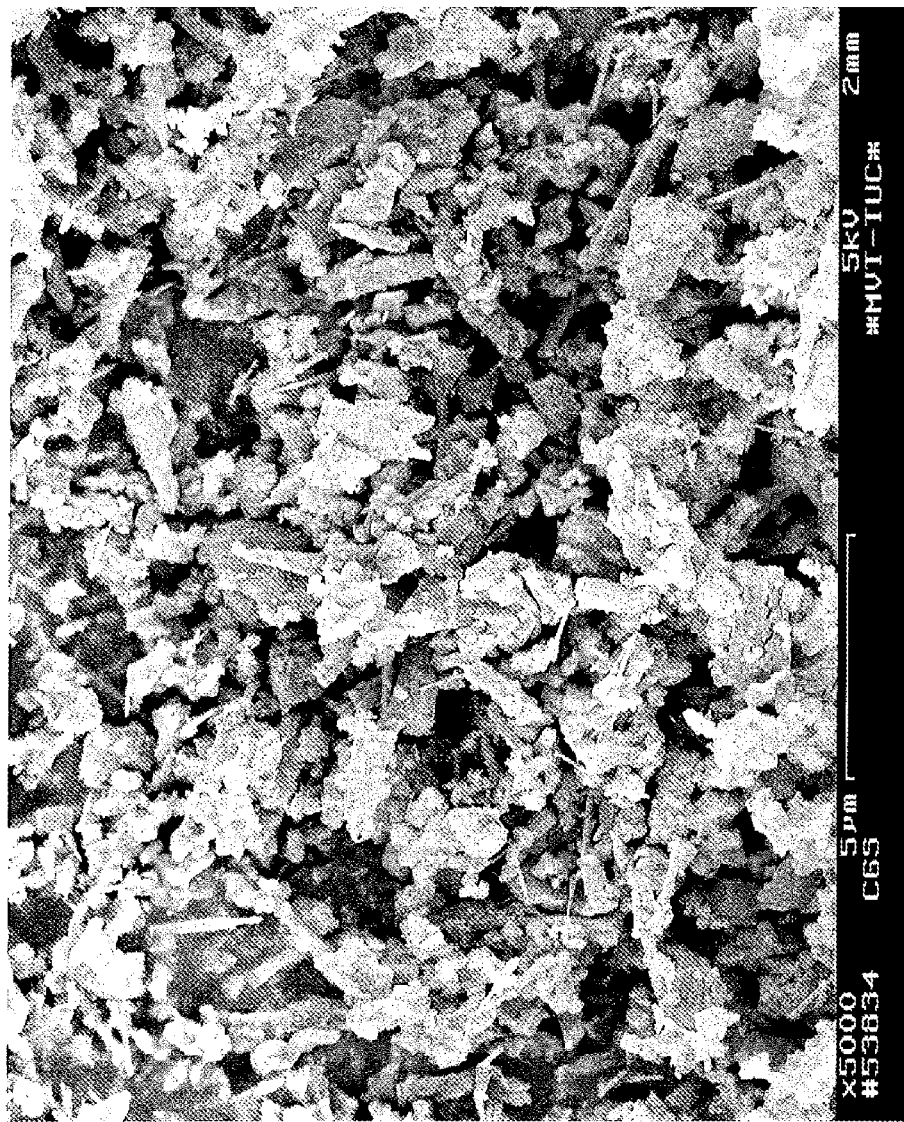
Figure 2B:
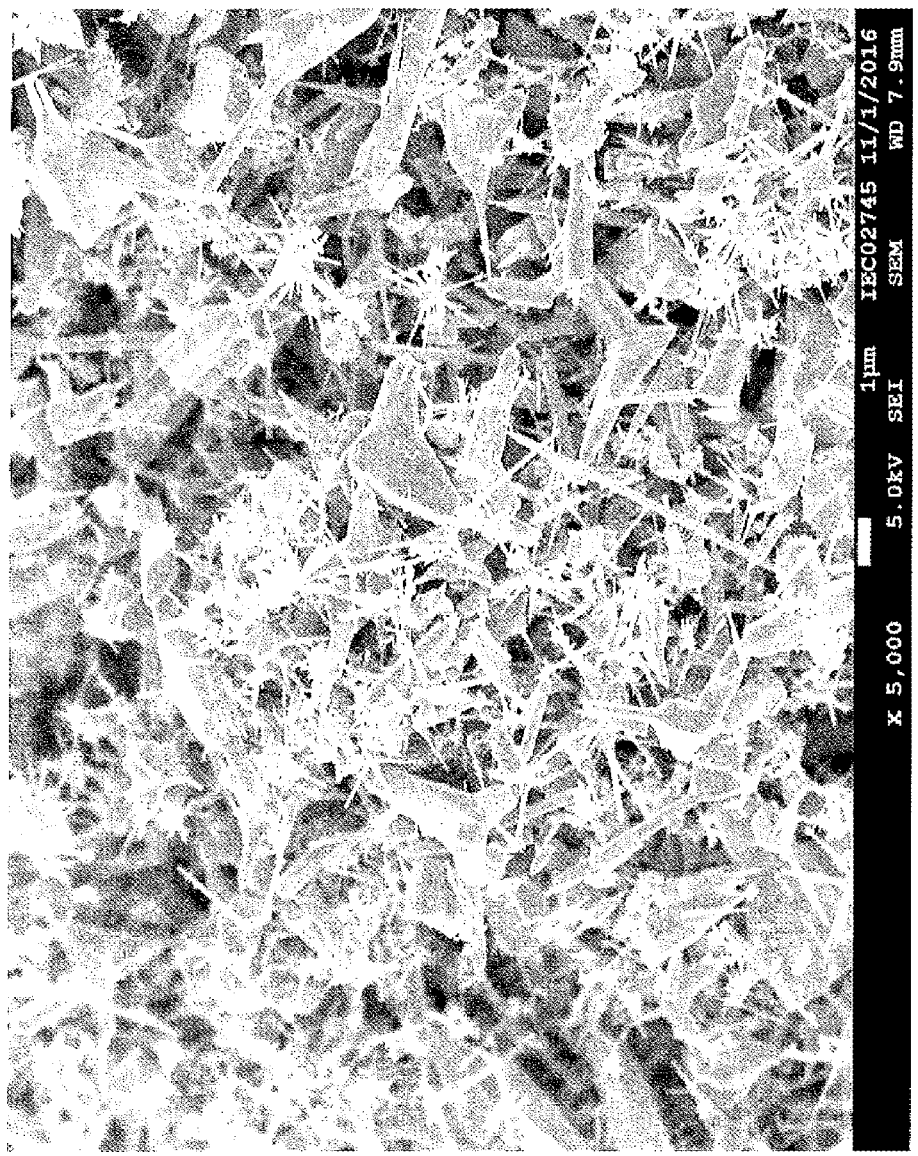
Figure 2C:
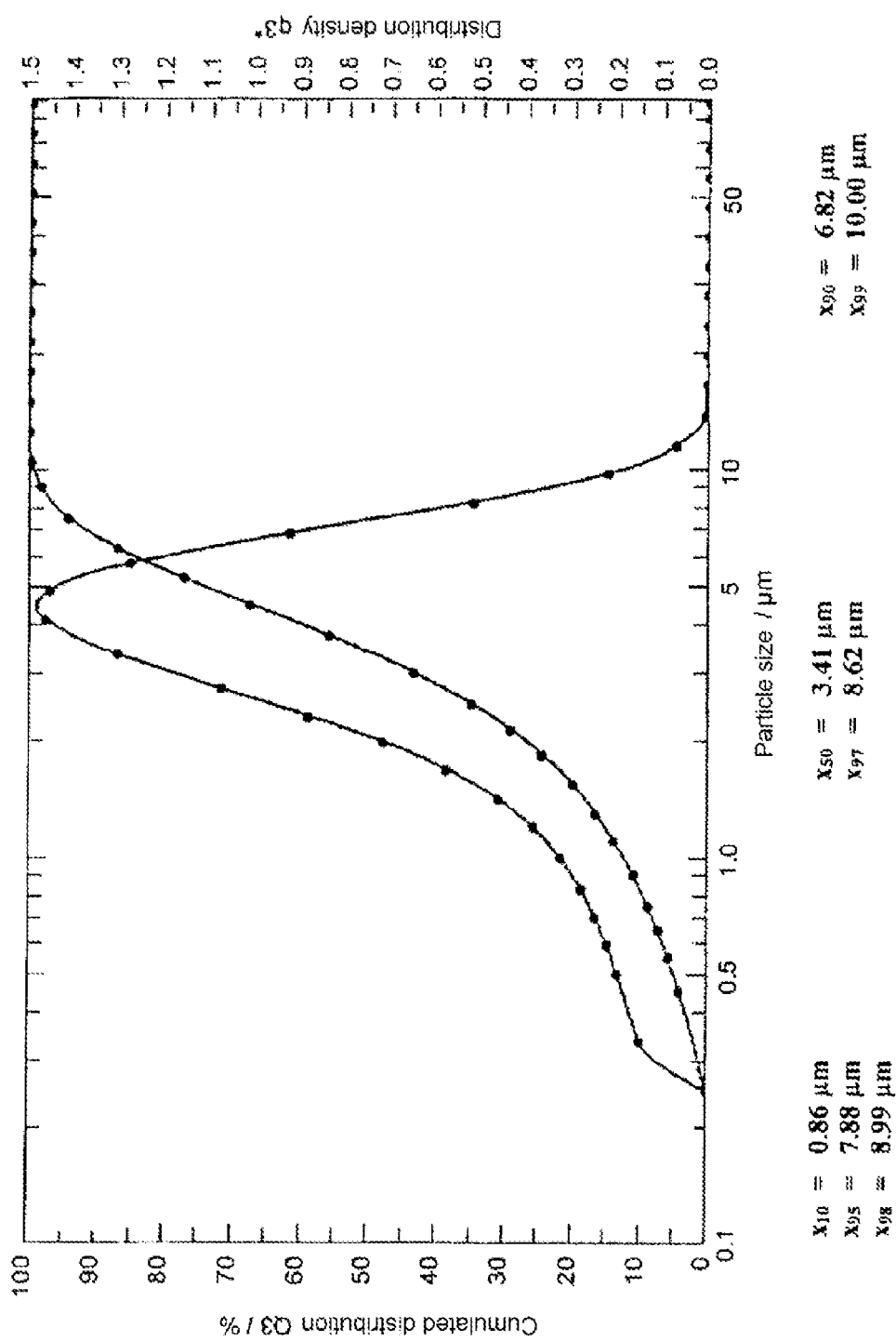

The particle size distribution of the process product according to the invention is also significantly narrower than has been previously obtainable, as can be seen from FIG. 2c. This clearly distinguishes the product according to the invention from known wet-chemically or dry-chemically produced products.

Due to the finely particulate nature and the comparatively uniform particle size, the metal chelate obtained by means of the process or the metal chelate composition according to the invention is readily meterable, easier to scatter and free-flowing and readily able to be dry mixed and dispersed. The fine microstructure can also have a positive effect on the resorbability of the products.

The metal chelate compound according to the invention is free of abraded material from mills and milling media.

The metal chelate compound is preferably completely free of chloride and/or sulfate ions as ligands.

The metal chelate composition is also preferably characterized in that the stoichiometric ratio (molar ratio) of chelating acid to metal compound, in the case of a chelate mixture based on each individual chelate compound, is from 0.5:1 to 4:1. In particular embodiments, the or at least one metal chelate compound present in the metal chelate composition according to the invention is a 2:1 amino acid-metal chelate compound, preferably of zinc or copper, or a 3:1 amino acid-metal chelate compound, preferably of iron or manganese.

As the analytical results reported below clearly show, the process of the invention makes it possible to obtain very well defined, chemically pure chelates, as examined with the aid of the IR spectra of selected metal-amino acid 1:2 chelates. Since amino acid chelates are particularly readily resorbable, or their constituents have a particularly high bioavailability, the high conversion and the chemical purity in respect of this product is a very important quality advantage of the products according to the invention. In addition, the quality is marked significantly by the absence of contamination of abraded metal, in particular since no milling media are used, and the particular morphology of the product.

In general, a wide variety of central atoms can be selected. In preferred embodiments, the metal of the metal chelate compound or at least one of the metal chelate compounds is selected from the group consisting of zinc (Zn), copper (Cu), manganese (Mn), selenium (Se), iron (Fe), calcium (Ca), magnesium (Mg), nickel (Ni), cobalt (Co), vanadium (V), chromium (Cr) and molybdenum (Mo).

In preferred embodiments, the chelating organic acid of the metal chelate composition according to the invention is selected from the group consisting of alpha-hydroxycarboxylic acids, beta-hydroxycarboxylic acids, natural amino acids, essential amino acids and synthetic amino acids.

The metal chelates of the invention in particular encompass the following substance types and substances: zinc bisglycinate, zinc bislysinate, zinc bismethionate, copper bisglycinate, copper bislysinate, copper bismethionate, (selenium methionate, selenium cysteinate), iron bisglycinate, iron trisglycinate, iron bislysinate, iron trislysinate, iron bismethionate, iron trismethionate, manganese bisglycinate, manganese trisglycinate, manganese bislysinate, manganese trislysinate, manganese bismethionate, managanese trismethionate.

The metal chelates of the invention can be used in a conventional way. In particular, the following uses will be mentioned here: in a feed additive, in a nutrient, as and in a nutrient supplement, as or in a nutrient additive, as or in a medicament, as or in an antiseptic, in a pharmaceutical composition, as or in a fermentation additive, as fertilizer additive, in a seed treatment agent, in a crop protection agent, as catalyst for chemical reactions or in an electroplating additive. The invention accordingly also encompasses compositions for the abovementioned uses, which have been prepared or formulated for these uses and contain the process product of the process of the invention, i.e. the metal chelate composition, as described in more detail above.

WORKING EXAMPLES

The effect according to the invention of the mechanochemical stressing of metal oxides, metal carbonates or metal oxalates together with in each case an organic acid, preferably amino acid, in a fluidized-bed opposed-jet mill will be illustrated below with the aid of a number of examples. Here, the reaction millings of the process of the invention are carried out by way of example on a 2 to 22 kilogram scale. This does not represent a limitation. In principle, it is also possible to realize considerably larger fluidized-bed opposed-jet mills as reactors for chelate production by modification of the dimensions, both for larger individual amounts of material introduced and also for continuous operation. Larger fluidized-bed opposed-jet mills for jet milling are already industrially available. The working examples reported are for a fluidized-bed opposed-jet mill from the manufacturer Hosokawa Alpine, Augsburg, having the designation AFG 100 and AFG 400, or from the manufacturer Netzsch, Hanau, having the designation CGS 10.

Working Example 1

1.501 kg of glycine (20.0 mol) and 0.814 kg of zinc oxide (10.0 mol) are milled together for a time of 45 minutes in a fluidized-bed opposed-jet mill at an air flow of 50-80 $m^3/h$, a milling gas pressure of 7.0 bar and a classifier rotational speed of 18 000 $s^{-1}$. An IR spectroscopic analysis of the end product (FIG. 4) shows the virtually complete conversion of the amino acid mentioned (>95%) into the corresponding zinc glycinate (synonyms according to Chemical Abstracts Service CAS: a) bis(glycinato-N,O)zinc, b) bis(glycinato)zinc, c) glycine zinc salt, d) glycine, zinc complex, e) zinc bisglycinate, f) zinc glycinate, g) zinc(II) glycinate, h) zinc, bis(glycinato)). This IR spectrum corresponds to that of a commercial reference, CAS: 14281-83-5).

Working Example 2

1.940 kg of methionine (13.0 mol) and 0.529 kg of zinc oxide (6.5 mol) are milled together for a time of 45 minutes in a fluidized-bed opposed-jet mill at an air flow of 50-80 $m^3/h$, a milling gas pressure of 7.0 bar and a classifier rotational speed of 18 000 $s^{-1}$. An IR spectroscopic analysis of the end product (FIG. 5) shows the virtually complete conversion of the amino acid mentioned (>95%) into the corresponding zinc methionate (Chemical Abstracts Number, CAS: 40816-51-1).

Working Example 3

1.900 kg of lysine (13.0 mol) and 0.529 kg of zinc oxide (6.5 mol) are milled together for a time of 45 minutes in a fluidized-bed opposed-jet mill at an air flow of 50-80 $m^3/h$, a milling gas pressure of 7.0 bar and a classifier rotational speed of 18 000 $s^{-1}$. The end product zinc lysinate is likewise obtained in a purity of >95%.

Working Example 4

1.576 kg of glycine (21.0 mol) and 0.835 kg of copper oxide (10.5 mol) are milled together for a time of 50 minutes in a fluidized-bed opposed-jet mill at an air flow of 50-80 $m^3/h$, a milling gas pressure of 7.0 bar and a classifier rotational speed of 18 000 $s^{-1}$. The end product copper glycinate is likewise obtained in a purity of >95%.

Working Example 5

1.791 kg of methionine (12.0 mol) and 0.477 kg of copper oxide (6.0 mol) are milled together for a time of 55 minutes in a fluidized-bed opposed-jet mill at an air flow of 50-80 $m^3/h$, a milling gas pressure of 7.0 bar and a classifier rotational speed of 18 000 $s^{-1}$. The end product copper methionate is likewise obtained in a purity of >95%.

Working Example 6

1.900 kg of lysine (13.0 mol) and 0.517 kg of copper oxide (6.5 mol) are milled together for a time of 50 minutes in a fluidized-bed opposed-jet mill at an air flow of 50-80 $m^3/h$, a milling gas pressure of 7.0 bar and a classifier rotational speed of 18 000 $s^{-1}$. The end product copper lysinate is likewise obtained in a purity of >95%.

Working Example 7

13.51 kg of glycine (180 mol) and 7.33 kg of zinc oxide (90 mol) are milled together for a time of 4.5 minutes in a fluidized-bed opposed-jet mill at an air flow of 800-1200 $m^3/h$, a milling gas pressure of 7.0 bar (80° C., uncooled compressor air) and a classifier rotational speed of 4650 $s^{-1}$. Characterization of the corresponding zinc glycinate was carried out by IR spectroscopy. The amount of product obtained corresponds to a throughput of 280 kg/h.

Figure 1B:
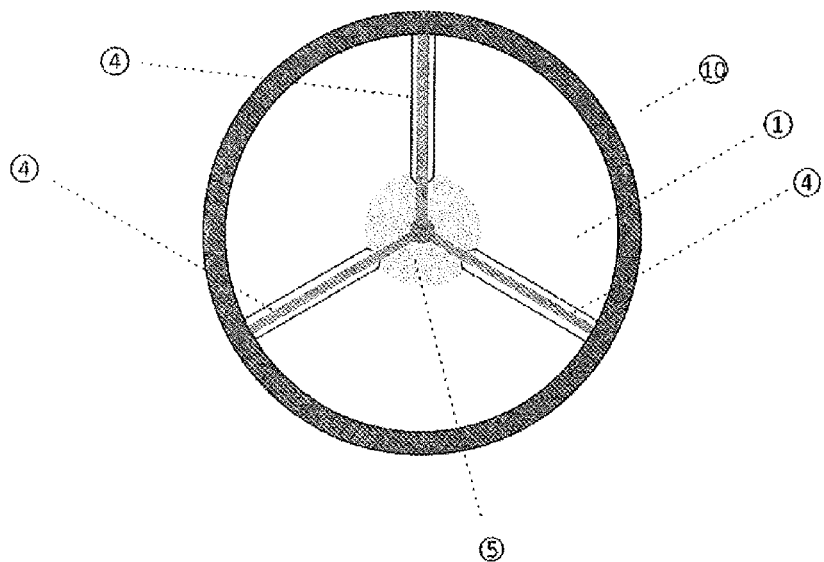
Figure 2D:
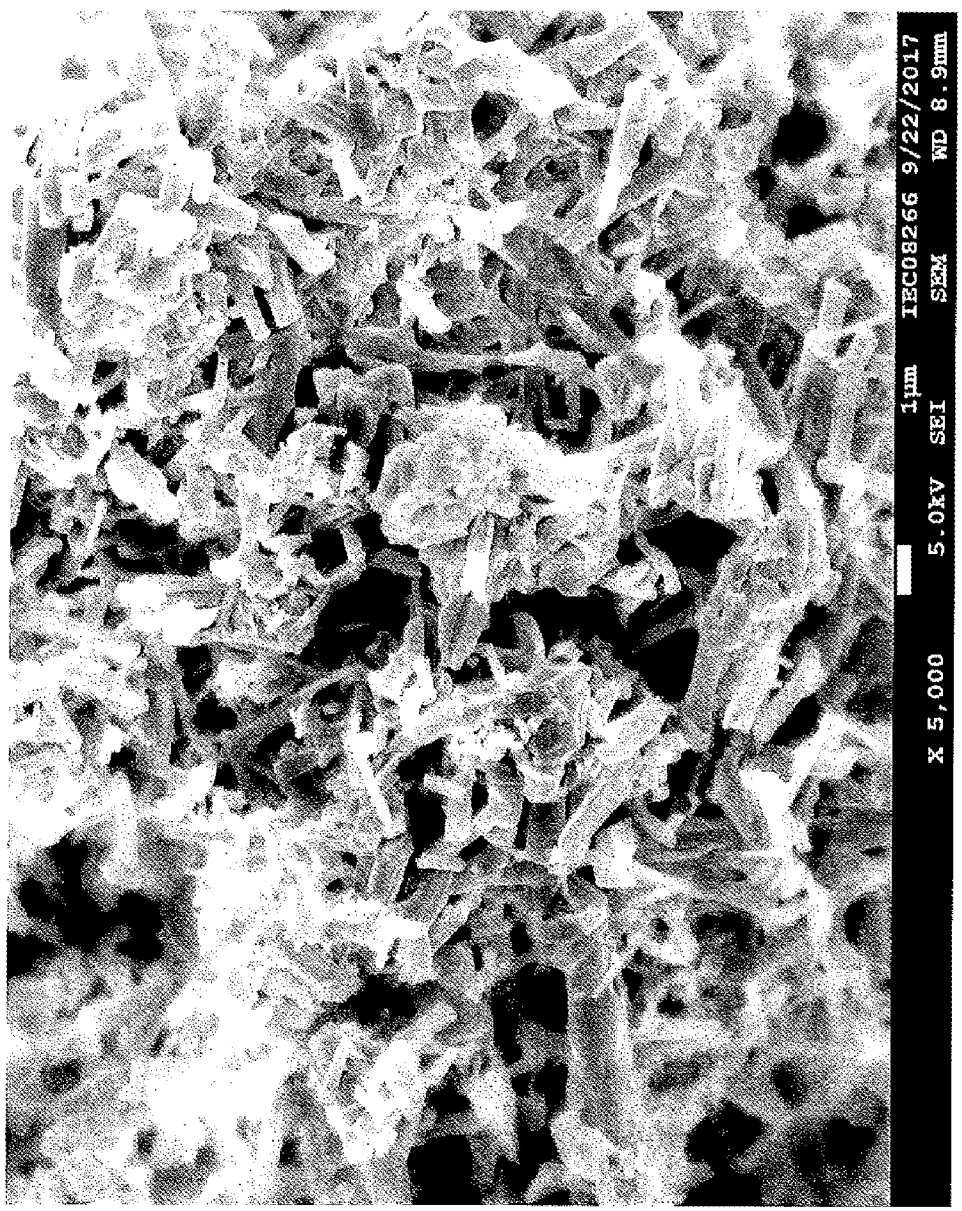

To better illustrate the invention, reference is made the accompanying figures. The figures show:

FIG. 1a: a sectional view from the side of an in-principle sketch of an apparatus for the reaction milling in a fluidized-bed opposed jet mill, FIG. 1b: a sectional view from above of an in-principle sketch of an apparatus for the reaction milling in a fluidized-bed opposed jet mill;

FIG. 2a: scanning electron micrograph of zinc-glycine chelate (at left),

FIG. 2b: scanning electron micrograph of zinc oxide (at right),

FIG. 2c: particle size distribution, measured on zinc bisglycinate,

FIG. 2d: scanning electron micrograph of copper glycinate

Figure 3:
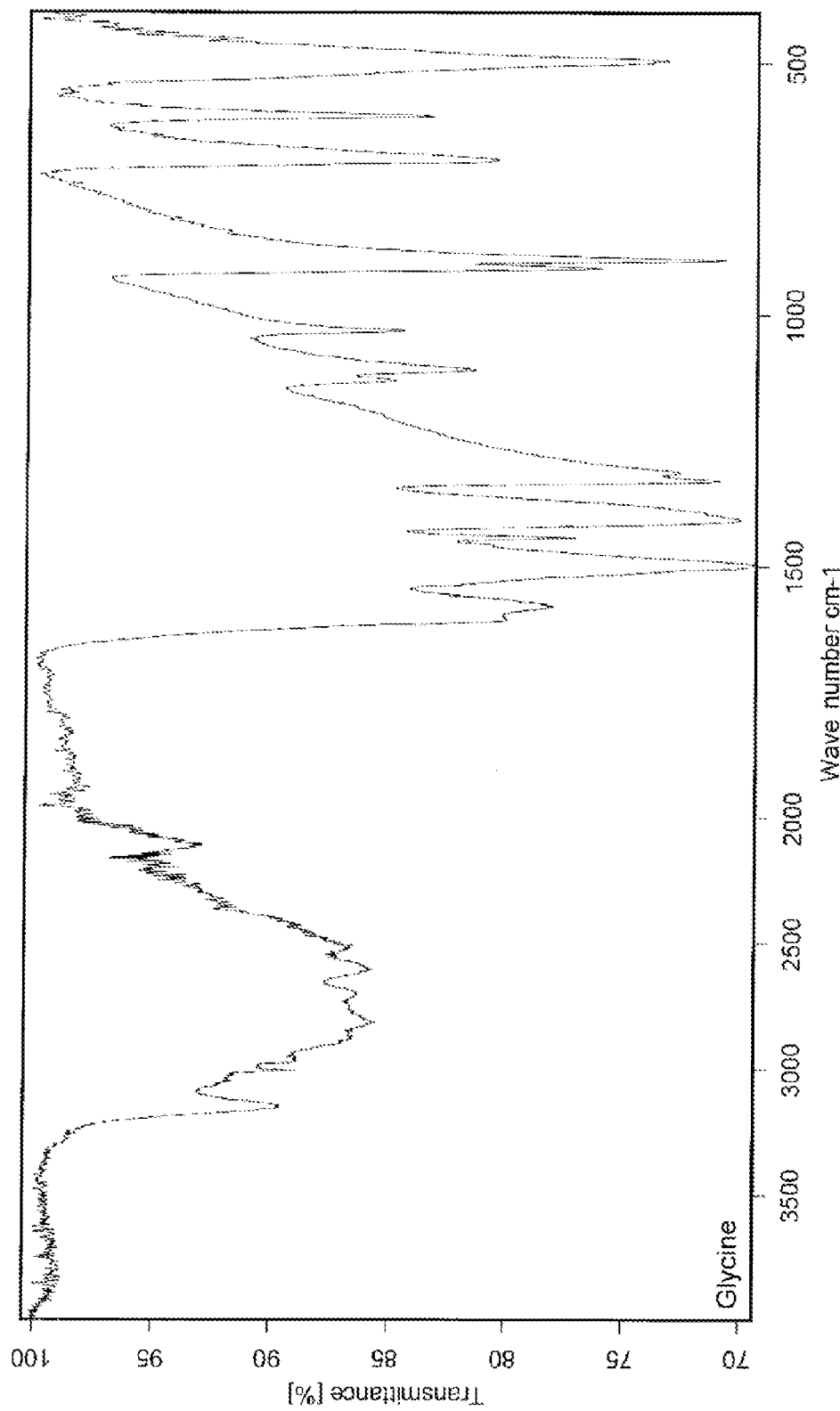
Figure 4:
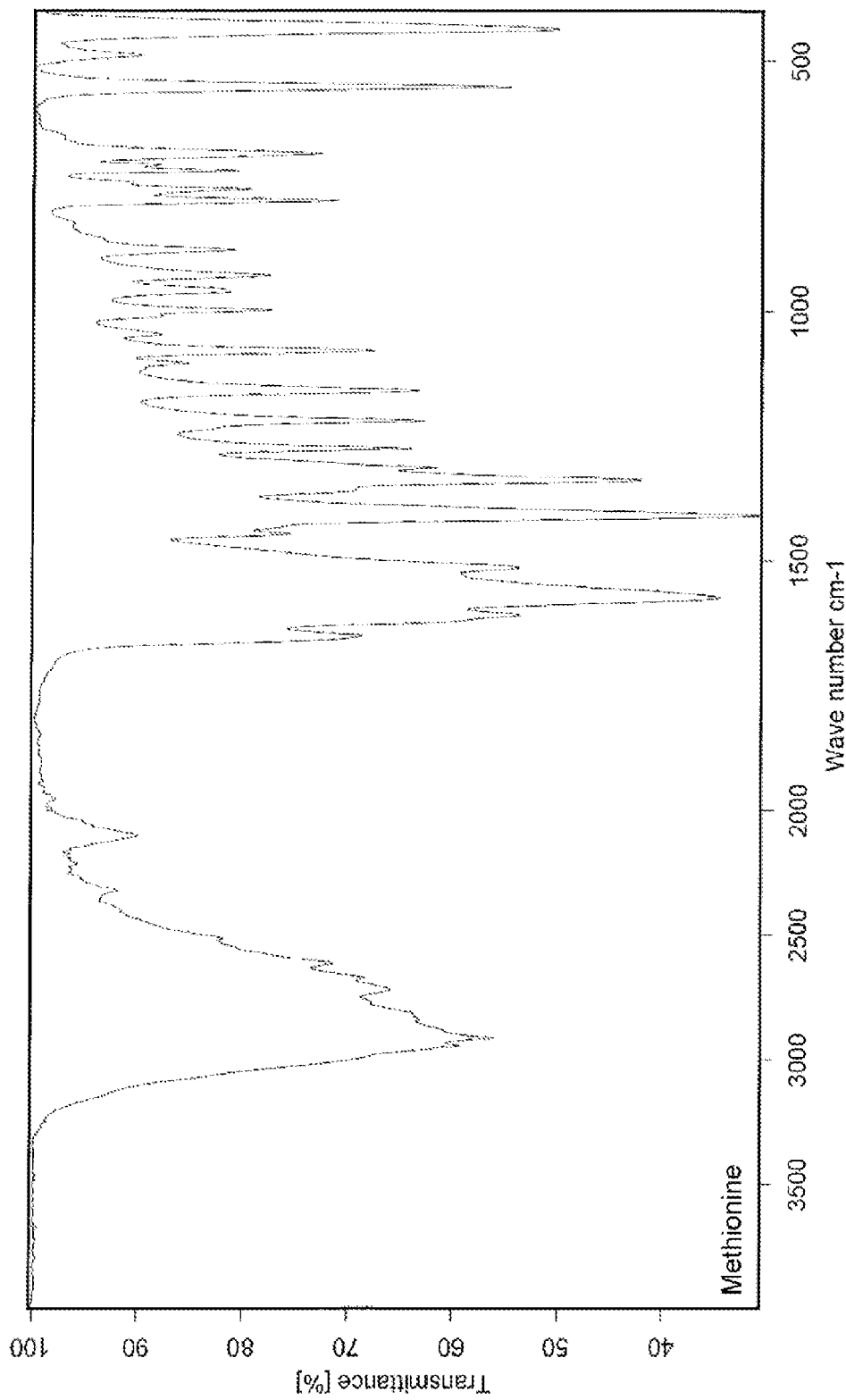
Figure 5:
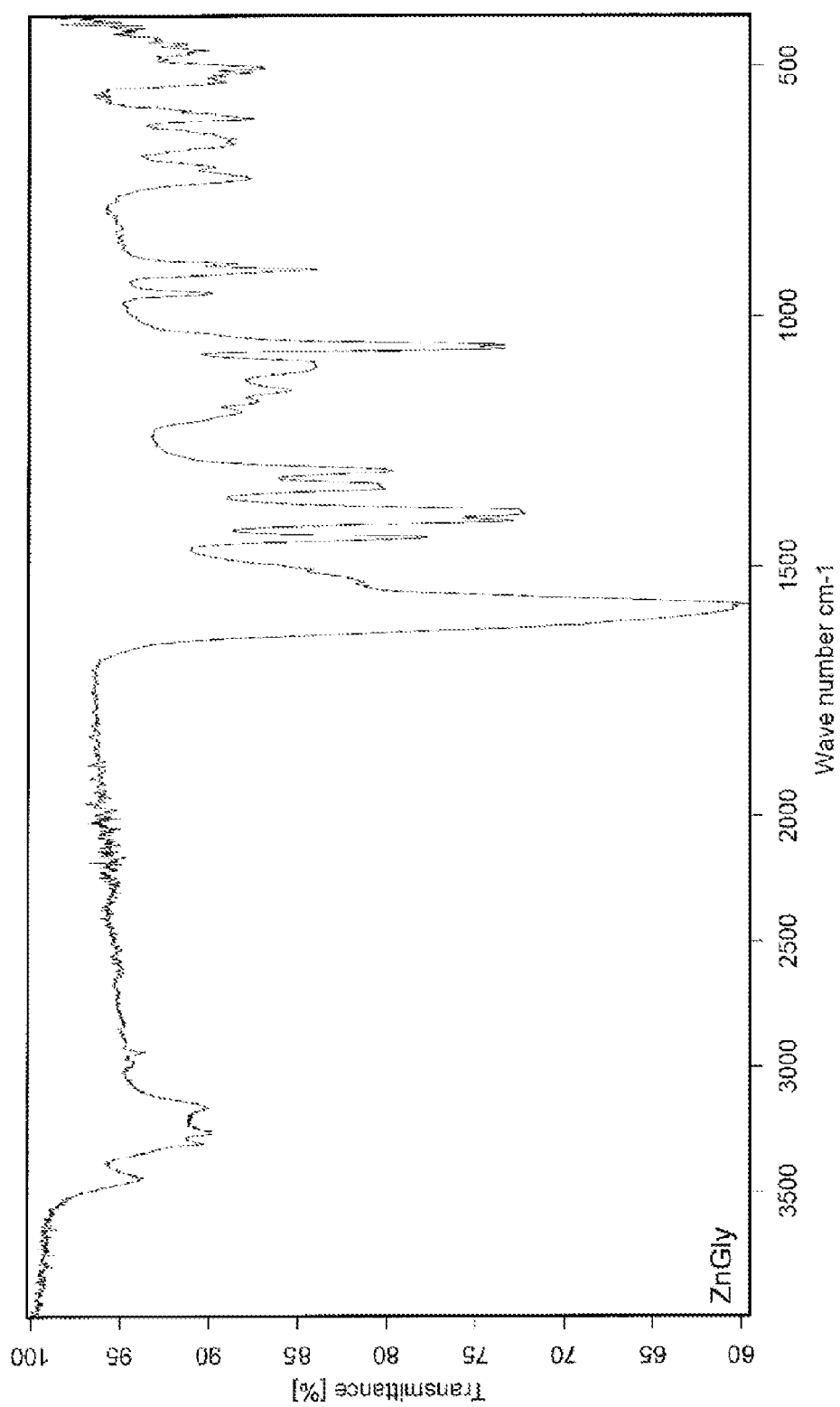
Figure 6:
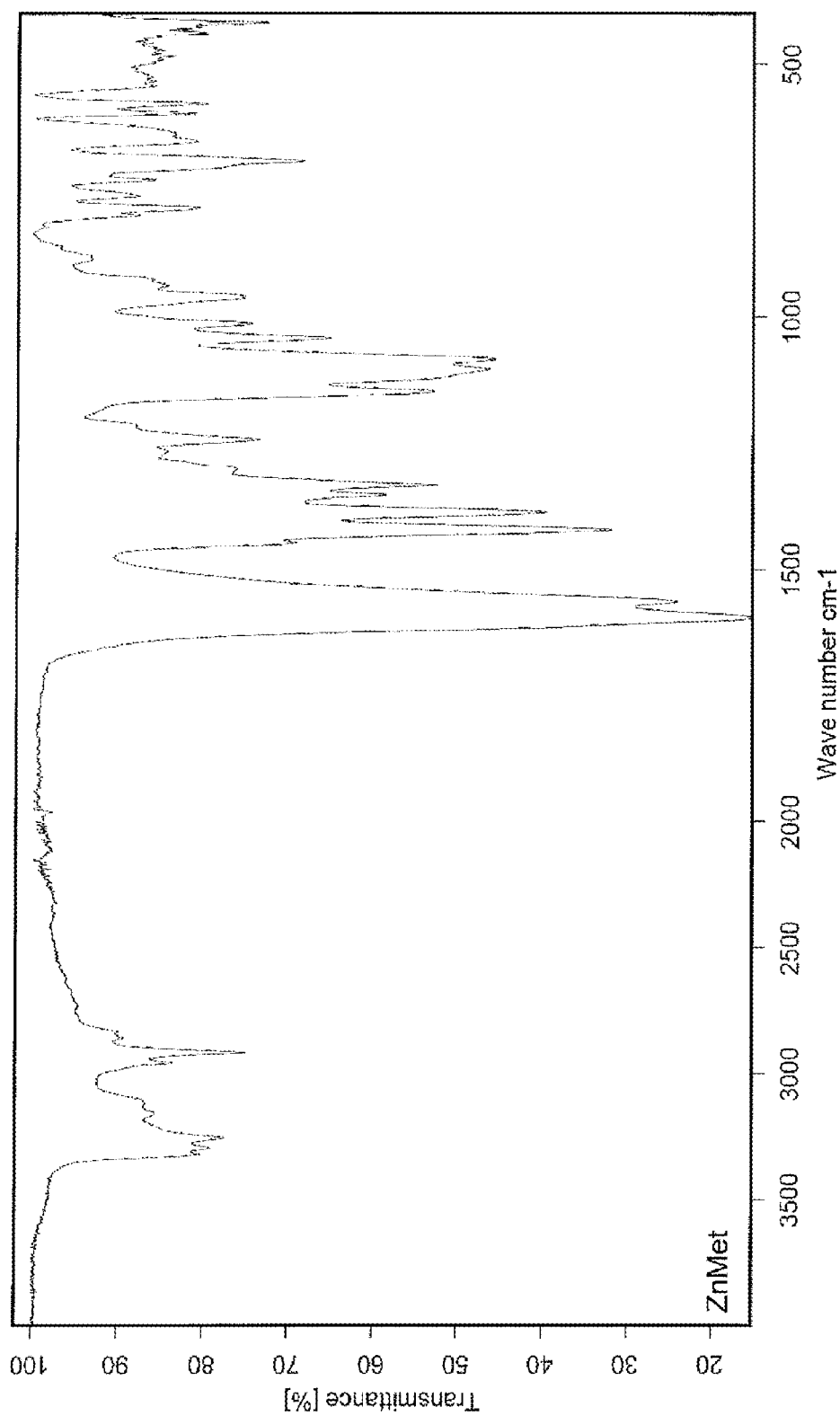
Figure 7:
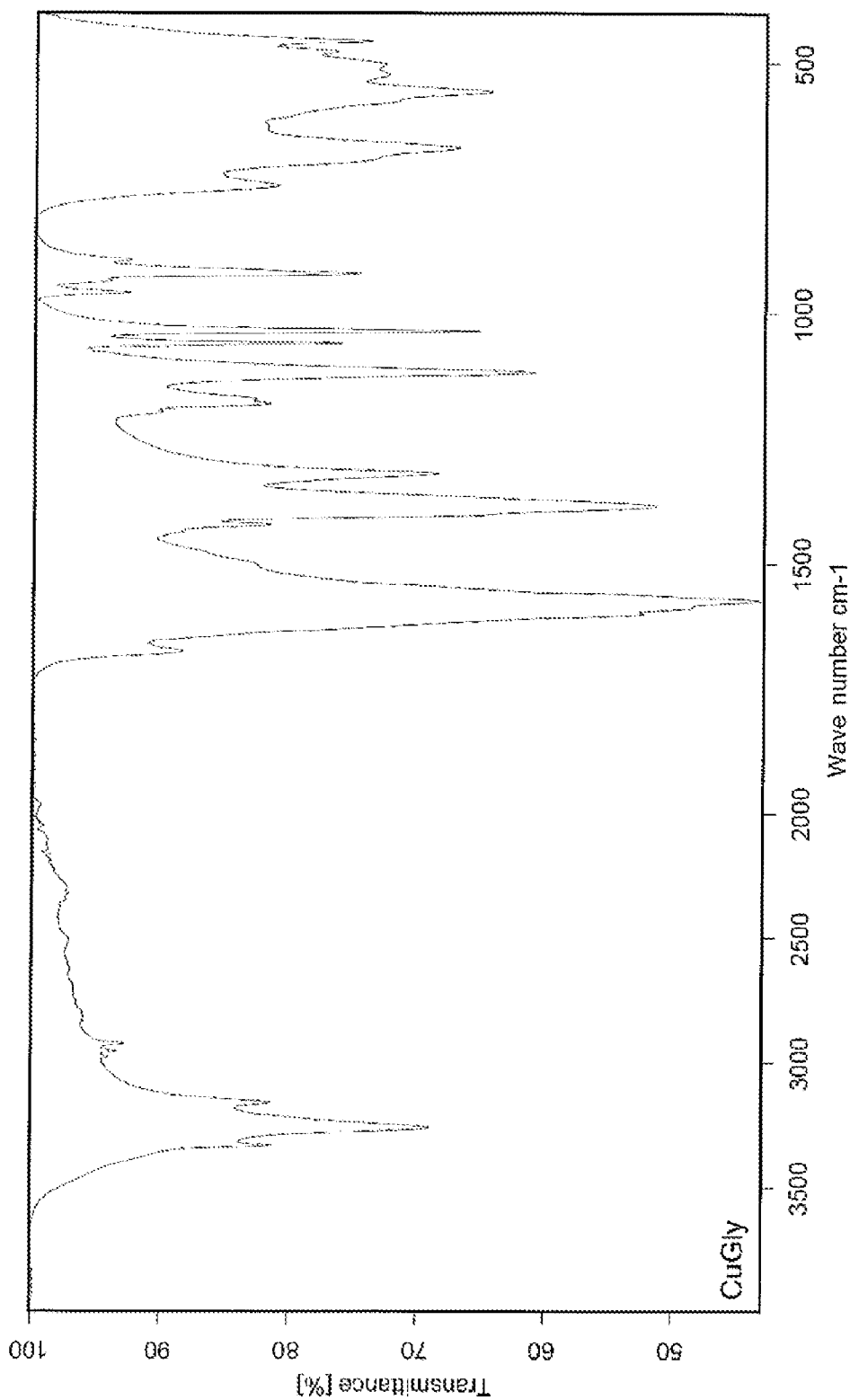

FIG. 3: ATR-IR spectrum of glycine;

FIG. 4: ATR-IR spectrum of methionine;

FIG. 5: ATR-IR spectrum of zinc-glycine chelate;

FIG. 6: ATR-IR spectrum of zinc-methionine chelate;

FIG. 7: ATR-IR spectrum of copper-glycine chelate.

FIGS. 1A and 1B show a schematic depiction of the reaction milling in a fluidized-bed opposed-jet mill 10, with the sketches being limited to the important elements of the apparatus. These are supplemented by apparatus elements which are not shown for starting material provision and introduction, product discharge, instrumentation and the like.

The fluidized-bed opposed-jet mill depicted is of the type which is commercially available and is used, for example, for very fine comminution of solids (milling, jet milling). In the example shown here, the mill is a fluidized-bed opposed-jet mill having a three-nozzle system.

FIG. 1a schematically shows the apparatus, namely the fluidized-bed opposed-jet mill 10, in a sectional view from the side, while FIG. 1b shows the same fluidized-bed opposed-jet mill 10 in a sectional view from above, depicting the nozzle arrangement. Identical parts are denoted by the same reference numerals.

As can be seen in FIG. 1a, a milling chamber 1 is connected via a feed conduit 2 to a milling stock reservoir 3 from which the milling stock is fed into the milling chamber 1. In this working example, the solid, premixed reaction milling stock is introduced from the reservoir 3 in free fall and thus without additional energy input through the feed conduit 2 into the milling chamber 1 which provides or comprises a reaction space 1 for the reaction milling according to the invention.

As an alternative, it would be possible to provide internals, for example distributing internals, and also additional transport means in the feed conduit 2, especially when introduction does not occur from above but instead, for example, from the side. Furthermore, it is possible in alternative embodiments not shown here to keep the reactants in stock in a plurality of separate reservoirs and mix them either immediately before the milling chamber 1, which can occur in one of the feed conduits 2 or in a separate mixing chamber, or to convey the reactants separately from the respective reservoirs and meter them into the milling chamber 1, where the mixing can occur within the milling chamber itself.

The fluidized-bed opposed-jet mill 10 has at least two fluid nozzles 4 which have to be directed toward one another or be arranged at an angle relative to one another in order to generate a collision zone in the center of the nozzle arrangement.

As can be seen from FIG. 1b, three fluid nozzles 4 for introduction of the milling jets are depicted in the example shown, with the nozzles or jet direction vectors crossing in a narrowly delimited zone where the particles collide and subsequently react with one another. The fluid nozzles 4 are arranged in a plane perpendicular to the plane of the drawing of FIG. 1a and lie in the plane of the drawing of FIG. 1b, oriented at angles of 120° relative to one another in each case. A fluidized bed 5 composed of milling stock and gas is formed in the center of the nozzle arrangement, i.e. in a collision zone which is formed by means of the gas jets leaving the fluid nozzles 4.

The milling stock particles present in each case in the center of the fluid nozzles 4 directed toward one another within the fluidized bed and the actual reaction space 5 formed thereby, here the reactants for the chelate formation reaction of the invention, are accelerated by the gas stream to such an extent that the chemical reaction and the associated product formation is triggered after the particle collisions.

The actual reaction space 5 in which the solid-state reaction takes place is located within the above-described collision zone in the fluidized bed.

FIG. 2a shows a scanning electron micrograph of a sample of a zinc glycinate (zinc bisglycinate) produced according to the invention compared to the zinc oxide (ZnO) used as starting material for the metal compound in FIG. 2b.

It can readily be seen that compact particles without a significant proportion of oversized particles, i.e. no needles as can be seen at right in FIG. 2b for the zinc oxide starting material, are formed by means of the process of the invention. As a result, the product displays better further processability and scatterability. The particle sizes are in a narrow one-figure micron range with a relatively narrow particle size distribution. The product is therefore very homogeneous and has a comparatively high surface area. The product can therefore be distributed readily, e.g. finely distributed in relatively complex compositions, and metered, but also readily compacted. Since no undesirable foreign salts and by-products are present, the amino acid density and metal density in the product are high.

The particle size distribution of the zinc bisglycinate produced as described in working example 1 and shown in FIG. 2a was examined more closely by means of laser light scattering. The results are shown in graph form in FIG. 2c.

The overwhelming proportion of the particles has a diameter in the range from about 1 to 4 μm. The narrow particle size distribution which can be read off from the individual diameter curve is reflected in typical ratios for the (volumetric) D10, D50 and D90 values.

99% of the particles have diameters of less than 10.00 μm ($D_{99}$),

90% of the particles have diameters of less than 6.82 μm ($D_{90}$),

50% of the particles have diameters of less than 3.41 μm ($D_{50}$) and

10% of the particles have diameters of less than 0.86 μm ($D_{10}$).

Further tests on other amino acid chelates according to the invention gave $D_{50}$ values in the range from 1 to 5 μm. $D_{50}$ is therefore preferably in the range from 1 to 5 μm, more preferably from 1.5 to 3.5 μm.

The D90 values are preferably in the range from 4 to 7 μm, and the D99 values were less than 15 μm in each of the cases examined.

FIG. 2d shows a scanning electron micrograph of a further product according to the invention, namely a copper bisglycinate produced as described in working example 4.

The micrographs of the various amino acid chelates (for $ZnGly_2$ and $CuGly_2$) very clearly demonstrate that the process uniformly gives homogeneous and finely divided amino acid chelates regardless of the starting compound.

FIGS. 3 to 7 show infrared spectra which will be discussed in more detail below.

Analytical Methods

In the case of the preparation according to the invention of amino acid-metal chelates, the analysis of such compounds and thus the proof of the occurrence of a (mechano) chemical reaction is carried out by means of characteristic band positions, band shapes and band intensities in the infrared spectrum (IR), see, for example, H. Güdnzler, H.-U. Gremlich, IR-Spektroskopie, 4$^{th}$ Edition, Wiley-VCH GmbH & Co. KGaA, Weinheim, 2003; G. Socrates, Infrared and Raman Characteristic Group Frequencies: Tables and Charts, third edition, John Wiley & Sons, 2004; R. M.

Silverstein, F. X. Webster, D. J. Kiemie, Spectrometric Identification of Organic Compounds, John Wiley & Sons, Inc., 2005; J. Liu, Y. Hou, S. Gao, M. Ji, R. Hu, Q. Shi, J. Therm. Anal. Calorim. 1999, 58, 323-330; M. Pedersen, H. D. Ashmead, U.S. Pat. No. 6,518,240 (B1) 2003; J. J.-C. Ko, S. X.-J. Xie, EP 2204099 (A1) 2010. This analysis is preferably carried out using the known technique of attenuated total reflection, thus as ATR-IR. This procedure allows direct measurement of a sample without any sample preparation and thus without contamination with auxiliaries (for example potassium bromide in the case of conventional sample preparation as KBr pellet) which could in turn influence the measurement, e.g. by reducing the measurement resolution by band broadening or falsification of the band shape (Christiansen effect). The latter undesirable effect caused by a particle size which is too large does not occur in the case of the product material produced according to the invention since this material occurs as compact particles in a small single-figure micron range with a comparatively large surface area (FIG. 2a, d).

The structural characterization of, for example, zinc bismethionate may be found in R. B. Wilson, P. de Meester and D. J. Hodgson, Inorg. Chem. 1977, 16, 1498-1502 or M. Rombach, M. Gelinky, H. Vahrenkamp, Inorg. Chim. Acta 2002, 334, 25-33. In the present case, too, it was demonstrated by means of such spectroscopic reference measurements that the products produced according to the invention are structurally the same as wet-chemically-produced reference material, sometimes commercially available. This is emphasized particularly because the "American Association of Feed Control Officials" (AAFCO) define such chelates as products of the reaction of a metal ion of a soluble metal salt with an amino acid (see, for example, S. D. Ashmead, M. Pedersen, U.S. Pat. No. 6,426,424 (B1) 2002). In particular, the chelate formation was demonstrated by significant changes in the IR spectrum during the course of the production process of the invention, which will be illustrated below with the aid of suitable examples.

ATR-IR Analysis, Spectroscopic Proof of Chelate Formation

In the course of IR analysis for the purpose of demonstrating the chelate formation when carrying out the process of the invention, the change in position of the nitrogen-hydrogen stretching vibration NH of the ammonium group is of particular importance. This band is shifted from about 3150 wave numbers (cm$^{-1}$, unit of the abscissa of the IR spectrum) in the case of the amino acid glycine (FIG. 3) or from less than 2950 cm$^{-1}$ in the case of methionine (FIG. 4) to about 3440 cm$^{-1}$ for zinc glycinate (FIG. 5) or about 3295 cm$^{-1}$ for zinc methionate (FIG. 6) by chelate formation. The wave number differences which occur demonstrate the participation of the nitrogen atom in complexation, thus chelate formation itself. Further bands in this region above 3000 cm$^{-1}$ are essentially attributable to the presence of water of crystallization. In addition, harmonics of intense fundamental vibrations of the upper fingerprint region are to be found there. The asymmetric carboxylate stretching vibration $v_{as}$ (COO$^-$) of the amino acids which is originally present appears at about 1575 cm$^{-1}$. Its position barely moves during the course of chelate formation. The position of the symmetric pendant of the carboxylate vibration $v_{sym}$(COO$^-$) also remains stable. Nevertheless, the formation of a chelate in the course of the reaction according to the invention can also be recognized unambiguously in this upper fingerprint region since only in the case of the free amino acid is a deformation vibration $\delta_{sym}$ (NH$_3^+$) at about 1500 cm$^{-1}$ detected (e.g. $\delta_{sym}$(NH$_3^+$, glycine): 1498 cm$^{-1}$, $\delta_{sym}$(NH$_3^+$, methionine): 1514 cm$^{-1}$, $\delta_{sym}$ (NH$_3^+$, lysine): 1511 cm$^{-1}$), but this disappears during the course of reaction milling and chelate formation. The respective metal-nitrogen vibration in these chelates is found at only low wave numbers in the lower fingerprint region, e.g. Met-N (zinc methionate) at 419 cm$^{-1}$, because of the relatively high atomic masses of the metals. The significant changes there in the IR spectrum of the metal chelates compared to the corresponding spectra of the free amino acids are likewise unambiguous evidence of chelate formation during the course of the process of the invention.

In the case of copper bisglycinate compared to the starting material glycine, signals are present at about 3330, 3260 and 3160 cm$^{-1}$ in the IR region of the chelate bands (cf. FIG. 7).

Summary of the Advantages of the Invention

The invention provides an energy-efficient process carried out in the absence of solvent for preparing amino acid-metal chelates. Energy savings compared to previous processes arise firstly from the fact that no wet-chemical reactions with subsequent drying are required. Although a mechanochemical reaction is realized, no milling media and additional masses, for example counterweights in the case of reactions in excentric vibratory mills, are required, as otherwise in the prior art. The process product is therefore kept free of abraded metal from the milling media. A mixture of the starting materials amino acid/hydroxycarboxylic acid and metal oxide, metal carbonate or metal oxalate fed in under atmospheric pressure is preferably converted mechanochemically into the corresponding metal chelate solely by means of the fluid jet (gas jet) in a fluidized-bed opposed-jet mill due to the particle collisions initiated by the gas streams. The energy efficiency also arises from the fact that the process of the invention operates solely by means of the milling gas jet without additional introduction of thermal energy, radiative energy or the like being necessary. The autogenous reaction process which is therefore novel for complete chemical conversion of the starting materials allows the combination of organic acids, preferably naturally occurring amino acids such as glycine, methionine or lysine, with oxides, carbonates or oxalates of trace element metals, in particular of zinc, copper, manganese, selenium, iron, calcium, magnesium, nickel, cobalt, vanadium, chromium or molybdenum. Sought-after fodder additives and nutritional supplements, e.g. zinc (bis)glycinate, zinc (bis)methionate, zinc (bis)lysinate, copper (bis)glycinate, copper (bis)methionate, copper (bis)lysinate and many more, are obtained in this way. The use of hydroxycarboxylic acids instead of amino acids, which is likewise possible, leads first and foremost to food additives; other (industrial) uses of such chelate compounds are known. The process product is obtained in very structurally homogeneous and very pure form. Thermal stressing or decomposition of the organic chelate ligands, in particular the amino acids, is avoided as is contamination by abraded material from mills and milling media.

In contrast to known processes using various mills, for example excentric vibratory mills, the fluidized-bed opposed-jet mill also works in continuous operation.

The water of reaction is removed together with the exiting milling gas without extra energy input.

LIST OF REFERENCE NUMERALS

10 Fluidized-bed opposed-jet mill
1 Milling chamber
2 Feed conduit
3 Milling stock reservoir
4 Fluid nozzle (milling gas nozzle)
5 Fluidized bed (reaction space)

The invention claimed is:
1. A process for preparing amino acid- or hydroxycarboxylic acid-metal chelates, comprising:
preparing a solvent-free mixture of
at least one metal compound from the group consisting of metal oxide, metal hydroxide and metal salt, and
at least one solid organic acid which comprises at least one chelating acid from the group consisting of alpha- and beta-amino acids and hydroxycarboxylic acids,
by introducing each of the at least one metal compound and the at least one solid organic compound in particulate form into a fluid jet of a fluidized-bed opposed-jet mill operating without milling media; and
subjecting the solvent-free mixture to mechanical stress in said fluidized-bed opposed-jet mill which is sufficient for causing mechanical activation of at least one of the at least one metal compound and the at least one solid organic acid by particle collision events within a reaction space formed in a jet region of the fluid jet which is sufficient for a solid-state reaction to form metal chelate particles wherein 90% of the metal chelate particles have a diameter of not more than 15 μm and 50% of the metal chelate particles have a diameter of not more than 5 μm.

2. The process as claimed in claim 1, wherein the fluidized bed and the reaction space is formed in a fluid stream section in a crossing region of a jet direction of at least two fluid nozzles.

3. The process as claimed in claim 1, wherein the fluidized-bed opposed-jet mill is operated at flow velocities ranging from about 300 to 1000 m/s, and at a milling gas pressure ranging from about 5 to 10 bar.

4. The process as claimed in claim 1 wherein each of the at least one metal compound and the at least one solid organic acid are transported by a transport device into a milling chamber and reach the reaction space in an interior of the milling chamber in free fall.

5. The process as claimed in claim 1 wherein a fluid in the fluid jet is a gas selected from the group consisting of air, nitrogen, argon, carbon dioxide, and steam, in each case either individually or in admixture.

6. The process as claimed in claim 1 wherein the at least one metal compound is a metal carbonate or metal oxalate.

7. The process as claimed in claim 1 wherein the at least one metal compound contains at least one metal or a mixture of metals selected from the group consisting of zinc (Zn), copper (Cu), manganese (Mn), selenium (Se), iron (Fe), calcium (Ca), magnesium (Mg), nickel (Ni), cobalt (Co), vanadium (V), chromium (Cr) and molybdenum (Mo).

8. The process as claimed in claim 1 wherein the subjecting step is performed such that 99.9% of the metal chelate particles have a diameter of not more than 25 μm.

* * * * *